(12) United States Patent
Dituri

(10) Patent No.: US 11,800,988 B1
(45) Date of Patent: Oct. 31, 2023

(54) SYSTEMS AND METHODS FOR MONITORING HEART RATE VARIABILITY

(71) Applicant: University of South Florida, Tampa, FL (US)

(72) Inventor: Joseph Dituri, Tampa, FL (US)

(73) Assignee: University of South Florida, Tampa, FL (US)

( * ) Notice: Subject to any disclaimer, the term of this patent is extended or adjusted under 35 U.S.C. 154(b) by 77 days.

(21) Appl. No.: 15/915,896

(22) Filed: Mar. 8, 2018

Related U.S. Application Data

(60) Provisional application No. 62/468,480, filed on Mar. 8, 2017.

(51) Int. Cl.
*A61B 5/024* (2006.01)
*A61B 5/00* (2006.01)
*A61B 5/282* (2021.01)
*A61B 5/352* (2021.01)

(52) U.S. Cl.
CPC .......... *A61B 5/02405* (2013.01); *A61B 5/282* (2021.01); *A61B 5/352* (2021.01); *A61B 5/6823* (2013.01); *A61B 5/6832* (2013.01); *A61B 5/746* (2013.01); *A61B 2562/164* (2013.01)

(58) Field of Classification Search
CPC ... A61B 5/02405; A61B 5/6823; A61B 5/746; A61B 5/04085; A61B 5/6832; A61B 5/0456; A61B 2562/164
See application file for complete search history.

(56) References Cited

U.S. PATENT DOCUMENTS 6,923,763 B1 8/2005 Kovatchev et al.
9,398,884 B2* 7/2016 Tanishima et al. .. A61B 5/1455
(Continued)

OTHER PUBLICATIONS

Cherry A, Forkner L, Frederick H, et al; Predictors of increased PaCO2 during immersed prone exercise at 4.7 ATA, J Appl Physiol 106: pp. 316-325, 2009. doi:10.1152/japplphysiol.00885.2007.
Edmond De Meersman, R; Heart rate variability and aerobic fitness American Heart Journal Volume 125, Issue 3, Mar. 1993, pp. 726-731.
Golinska "Poincaré Plots in Analysis of Selected Biomedical Signals" ISBN (Year: 2013).*
Gunduz et al., Heart rate variability and heart rate turbulence in patients with chronic obstructive pulmonary disease, Via Medica, Cardiology Journal, 2009, Vol. 16, pp. 553-559.
(Continued)

*Primary Examiner* — Amy R Weisberg
(74) *Attorney, Agent, or Firm* — QUARLES & BRADY LLP

(57) ABSTRACT

In one embodiment, a system for monitoring heart rate variability including an electrode configured to be placed against a user's chest and generate heart beat data and a data collection and processing device that receives the heart beat data from the electrode, the data collection and processing device being configured to execute a heart rate variability program configured to continually determine the user's heart rate variability in real time based upon the heart beat data and to determine whether or not the user is in physiological distress based upon the determined heart rate variability.

22 Claims, 4 Drawing Sheets

(56) References Cited

U.S. PATENT DOCUMENTS

| | | | |
|---|---|---|---|
| 9,655,532 B2* | 5/2017 | Blake et al. | A61B 5/02405 |
| 10,022,057 B1* | 7/2018 | Blake et al. | A61B 5/6831 |
| 2012/0108917 A1* | 5/2012 | Libbus et al. | A61B 5/0006 600/301 |
| 2012/0123232 A1 | 5/2012 | Najarian et al. | |
| 2015/0351690 A1* | 12/2015 | Toth et al. | A61B 5/6833 600/373 |
| 2016/0367157 A1* | 12/2016 | Blake et al. | A61B 5/02405 |
| 2017/0333664 A1* | 11/2017 | Luo et al. | A61B 5/316 |
| 2019/0022400 A1* | 1/2019 | Kumar et al. | A61B 5/0205 |

OTHER PUBLICATIONS

Heathers J., Everything Hertz: methodological issues in short-term frequency-domain HRV. Frontiers in Physiology, http://doi.org/10.3389/fphys., May 2014, volume 5, Article 177, pp. 1-15.

Jonathan, E., and Martin Leahy, Investigating a smartphone imaging unit for photoplethysmography, Physiological Measurement 31.11 (2010): N79-N83.

Joseph Dituri, Heart Rate Variability Analysis as a Means of Real-time Hypercapnia Detection, University of South Florida, College of Chemical & Biomedical Engineering, Nov. 10, 2016, pp. 1-14.

Levy W, Cerqueira M, Harp G, et al; Effect of endurance exercise training on heart rate variability at rest in healthy young and older men, The American Journal of Cardiology, Volume 82, Issue 10, Nov. 15, 1998, pp. 1236-1241.

McCraty, R. Shaffer, F., Heart Rate Variability: New Perspectives on Physiological Mechanisms, Assessment of Self-regulatory Capacity, and Health risk, Glob Adv Health Med. Jan. 2015; 4(1): pp. 46-61.

Niskanen et al., Software for advanced HRV analysis, University of Kuopio Department of Applied Physics Report Series ISSN 0788-4672, 4.9.2002, Report No. 2/2002, pp. 1-11.

Pöyhönen M, Syväoja S, Hartikainen J, et al; The effect of carbon dioxide, respiratory rate and tidal volume on human heart rate variability. Acta Anaesthesiologica Scandinavica, 2004 - 48: 93-101. doi:10.1111/j.1399-6576.2004.00272.x.

Pilla R, Landon C, Dean J, A Potential Early Physiological marker for CNS Oxygen Toxicity; hyperoxic hyperpnea precedes seizure in unanesthetized rats breathing hyperbaric oxygen, J Appl Physiol 114: 2013, pp. 1009-1020.

Stein P, Ehsani A, Domitrovich P, et al; Effect of exercise training on heart rate variability in healthy older adults American Heart Journal Volume 138, Issue 3, Sep. 1999, pp. 567-576.

Tarvainen et al., Kubios HRV- Heart rate variability analysis software, www.intl.elsevierhealth.com/journals/cmpb, Computer Methods and Programs in Biomedicine 113 (2014), pp. 210-220.

Volterrani M, Scalvini S, Mazzuero G, et al. Decreased heart rate variability in patients with chronic obstructive pulmonary disease, Chest. 1994;106(5): pp. 1432-1437.

Cooke W, Salinas J, Convertino V, et al, Heart Rate Variability and Its Association with Mortality in Prehospital Trauma Patients, Journal of Trauma-Injury Infection & Critical Care: Feb. 2006 - Volume 60 - Issue 2 - pp. 363-370.

\* cited by examiner

SYSTEMS AND METHODS FOR MONITORING HEART RATE VARIABILITY

CROSS-REFERENCE TO RELATED APPLICATION

This application claims priority to co-pending U.S. Provisional Application Serial No. 62/468,480, filed Mar. 8, 2017, which is hereby incorporated by reference herein in its entirety.

BACKGROUND

Hypercapnia is a condition in which there are abnormally elevated carbon dioxide ($CO_2$) levels in the blood. Such a condition can occur in various circumstances. For example, divers who use rebreathers can experience hypercapnia when the rebreather fails to absorb the $CO_2$ of the diver's exhaled breath. Hypercapnia can also occur in cases in which high levels of $CO_2$ are present in the ambient air in which a person breathes. As $CO_2$ is odorless and colorless, such a person may not realize he or she is breathing in excessive levels of $CO_2$. Hypercapnia can also occur in cases of extubation failure in which case a previously intubated patient cannot get sufficient oxygen.

If one experiences hypercapnia for an extended period of time, injury, including death, can occur. Given the potentially grave consequences of hypercapnia, it is critical to detect its onset as early as possible, preferably before symptoms appear. Currently, the most accurate way in which hypercapnia is detected is by performing an arterial blood gas panel in which the acidity (pH) and the levels of oxygen ($O_2$) and $CO_2$ in the blood from an artery are determined. While such a procedure is effective in revealing blood $CO_2$ levels, the procedure is invasive, time-intensive, and requires specialized equipment to perform chemical analysis of the individual's blood. What is needed is a simple, non-invasive, real-time, continuous means for determining when an individual is experiencing hypercapnia.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, needed is a simple, non-invasive, real-time, continuous means for determining when an individual is progressing towards and/or experiencing hypercapnia. Disclosed herein are systems and methods for monitoring an individual's heart rate variability, which can provide an indication of physiological stress placed on the individual, including conditions such as hypercapnia. In some embodiments, a system includes electrodes that can be applied to the individual's chest and a device that can determine the variability in the individual's heart rate. In some embodiments, an alert can be generated for the individual or persons caring for the individual when the individual's heart rate variability falls below a particular threshold, which is indicative of physiological stress on the individual.

In the following disclosure, various specific embodiments are described. It is to be understood that those embodiments are example implementations of the disclosed inventions and that alternative embodiments are possible. All such embodiments are intended to fall within the scope of this disclosure.

Heart rate variability is the temporal variation in frequency intervals between adjacent heartbeats and is related to some of the body's key regulatory systems and ultimately, health. Sympathetic and parasympathetic systems effect these temporal variations. Specifically, an optimal level of heart rate variability reflects healthy function and an inherent self-regulatory capacity, adaptability, or resilience. Generally speaking, greater heart rate variability is an indicator of better health and less physiological stress, while lesser variability indicates a pathology or poor function in levels of self-regulatory control systems.

While heart rate variability can be measured using a 12-lead electrocardiogram (ECG) machine in a clinical setting, such as a hospital, doctor's office, or clinic, such a machine cannot be used in one's daily life. Needed is a portable system that can be carried with the user to monitor the beating of the heart (i.e., the QRS complex timing) and discern the heart rate variability (i.e., frequency or temporal variability) by detecting the time between each R wave (R) and subsequent R wave (R+1). Most useful would be a device that can be worn by the user while carrying out normal activities. Such a device ideally would have sufficient power to operate for extended periods of time (e.g., up to 24 hours) and collect the data required for real-time analysis and user feedback.

Figure 1:
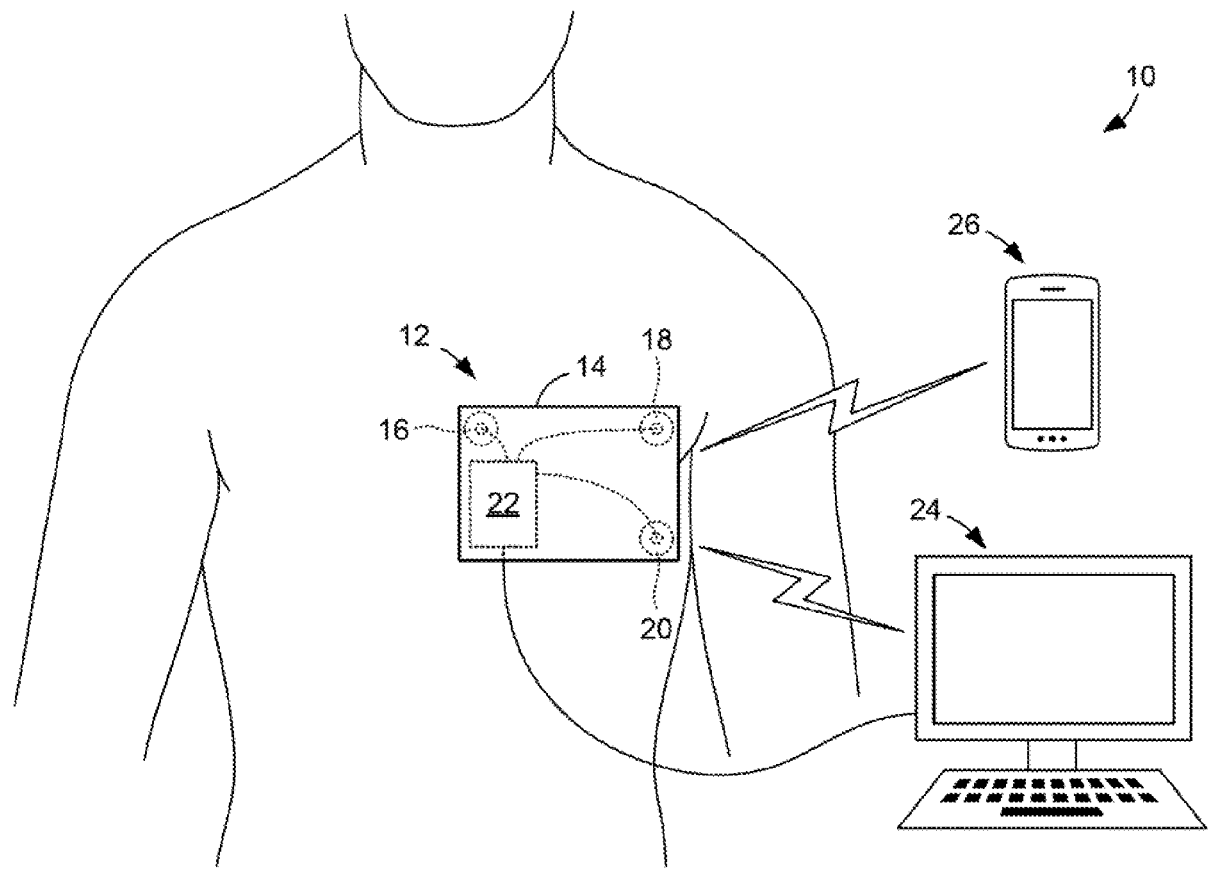
FIG. 1 is a schematic view of an embodiment of a system for monitoring heart rate variability.

FIG. 1 illustrates an example heart rate variability system 10 that satisfies the requirements identified above. As shown in FIG. 1, the system 10 is integrated into a patch 12 that can be worn by the user who is to be monitored. In some embodiments, the patch 12 is configured as a thin, flexible sheet 14 of material, such as neoprene and/or rubber, having adhesive on one side that can be used to secure the patch to the user's chest, as illustrated in FIG. 1. In some embodiments, the sheet 14 of material is approximately 4 inches tall and 6 inches wide. Integrated with the patch 12 are three ECG electrodes 16, 18, and 20 that can be used as sensors that sense the user's heart beats. One of these electrodes 20 is positioned at the lower right corner of the patch 12 (from the perspective of FIG. 1) so as to be located on the left side at the mid-axillary line within the fifth intercostal space of the user when the patch is worn. This positioning yields the highest and most discernible R wave output of the QRS complex. As shown in FIG. 1, the other electrodes 16 and 18 can be positioned at the upper corners of the patch 12 so as to be located at the left and right sides of the upper part of the user's left-side chest.

Each of the electrodes 16-20 is in electrical communication with a data collection and processing device 22 that is also integrated into the patch 12. By way of example, the electrodes 16-20 are connected to the data collection and processing device 22 with various electrical conductors, such as wires. In some embodiments, the data collection and processing device 22 is a small, rectangular component (e.g., approximately 3 inches long, 3 inches wide, and ½ inch deep) that is positioned in an unobtrusive position within the patch 12 and on the chest. As its name suggests, the data collection and processing device 22 collects and processes the heart beat data sensed by the electrodes 16-20.

Also shown in FIG. 1 are independent computing devices in the form of a desktop computer 24 and a smart phone 26. As illustrated in FIG. 1, the data collection and processing device 22 can communicate with these devices either wirelessly or through a wired connection. In some embodiments, alerts generated by the device 22 can be transmitted to one or more of these computing devices to warn the user, the user's physician, or the user's caregiver about a potential hypercapnia condition.

Figure 2:
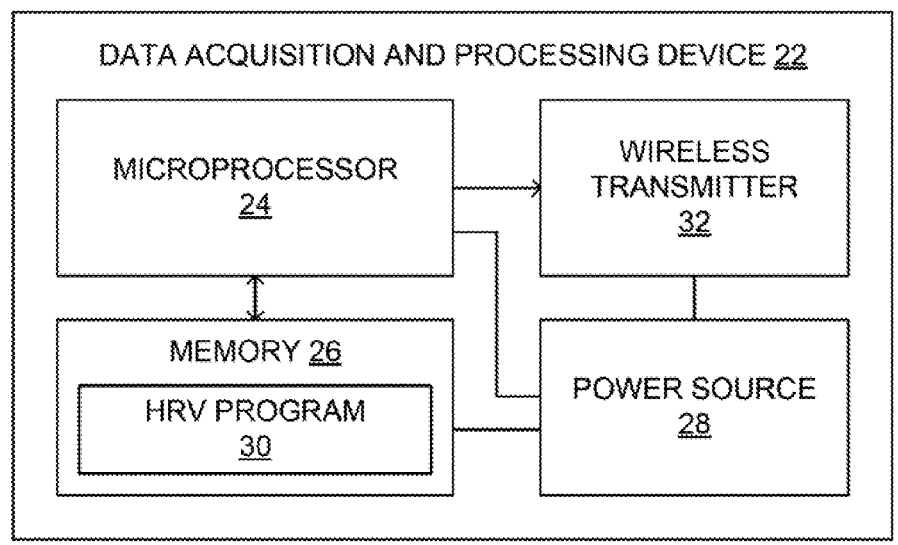
FIG. 2 is a block diagram of an embodiment of a data collection and processing device shown in FIG. 1.

FIG. 2 illustrates an example configuration for the data collection and processing device 22. As shown in this figure, the data collection and processing device 22 at least comprises a microprocessor 24, memory 26 (i.e., a non-transitory computer-readable medium which can, in some embodiments, be integrated with the microprocessor), and a power source 28, such as a battery. The microprocessor 24 controls the overall operation of the data collection and processing device 22, including the storage and analysis of the data sensed by the electrodes 16–20. In some embodiments, the microprocessor 24 executes a heart rate variability program 30 (logic comprising computer executable instructions) that comprises one or more heart rate variability algorithms that are configured to determine the heart rate variability of the user and determine, based upon that heart rate variability, the health of the user. As is further shown in FIG. 2, the data collection and processing device 22 can further include a wireless transmitter 32 that can be used to send wireless communications about the user's health.

In some embodiments, the data collection and processing device 22 can include other components, such as a simple user interface. Such a user interface can comprise components that can be used to control operation of the system 10, such as one or more buttons or switches. In addition, the user interface can comprise components that can be used to convey information to the user. Such components can comprise one or more of a display, lights, a speaker, and a vibratory device. As noted above, alerts generated by the data collection and processing device 22 can be transmitted to the independent computing devices, such as the computer 24 and the smart phone 26. In some embodiments, the alert can include graphical information that can be displayed on the independent computing devices to assist the observer in understanding the severity of the problem. In further embodiments, the heart rate data collected by the data collection and processing device 22 can be transmitted to the independent computing devices in real time and the analysis of the data can be performed on those computing devices in addition to or in lieu of the data collection and processing device 22 performing the analysis. In such a case, a version of the heart rate variability program 30 can also be resident on the computing devices.

As noted above, the data collection and processing device 22 is configured to analyze the heart rate data sensed by the electrodes 16-20. Among other things, the data collection and processing device 22 determines the temporal spacing of successive R waves to determine heart rate variability and, from that variability, makes a determination as to the user's health. In some embodiments, the data collection and processing device 20 evaluates the heart rate variability by generating Poincare plots. A Poincare plot is a graph that plots the time between successive R wave peaks as individual data points.

Figure 3A:
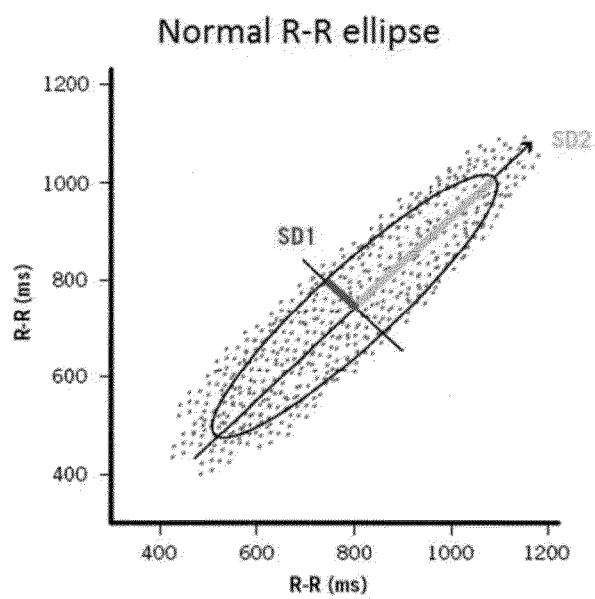
FIGS. 3A and 3B are Poincare plots that plot R wave intervals for healthy and unhealthy individuals, respectively.
Figure 3B:
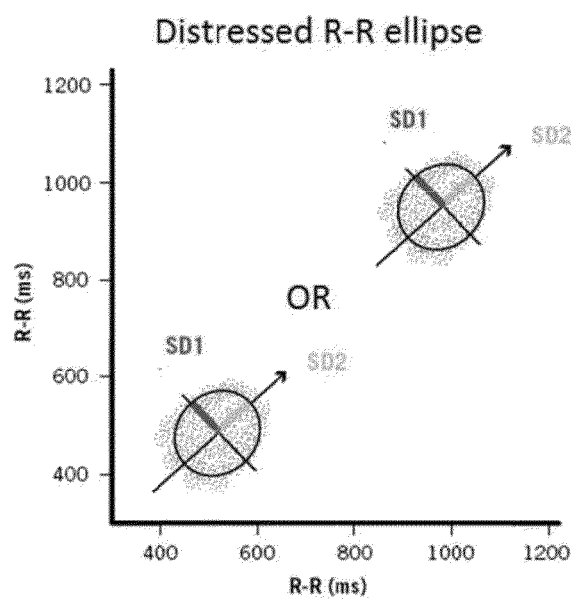

FIGS. 3A and 3B are examples of such plots. Each data point in these plots represents the time between two successive R wave peaks. As is apparent from FIG. 3A, which shows a Poincare plot for a healthy individual, the data points are generally dispersed within an ellipse having a transverse axis and a longitudinal axis. The portion of the transverse axis extending from the longitudinal axis is referred to as the line of identity and is termed SD1. The dispersion of all data points along the line of identity is termed SD2. As is apparent from FIG. 3A, in a Poincare plot for a healthy person, SD2 is approximately four times the length of SD1. This indicates relatively large heart rate variability. As is apparent from FIG. 3B, however, the SD2 in both ellipses (two different examples) is approximately the same length as SD1. This indicates less heart rate variability and, therefore, physiological stress, such as hypercapnia. During operation of the data collection and processing device 22, the ratio between SD1 and SD2 (e.g., SD2:SD1) can be continually calculated and compared to the "normal" (healthy) ratio for the purpose of evaluating the user's health. In some embodiments, what is a "normal" SD2:SD1 ratio can be determined during a calibration process in which the individual user's SD2:SD1 ratio when the user is healthy is monitored and designated as the normal or "control" SD2:SD1 ratio.

Figure 4A:
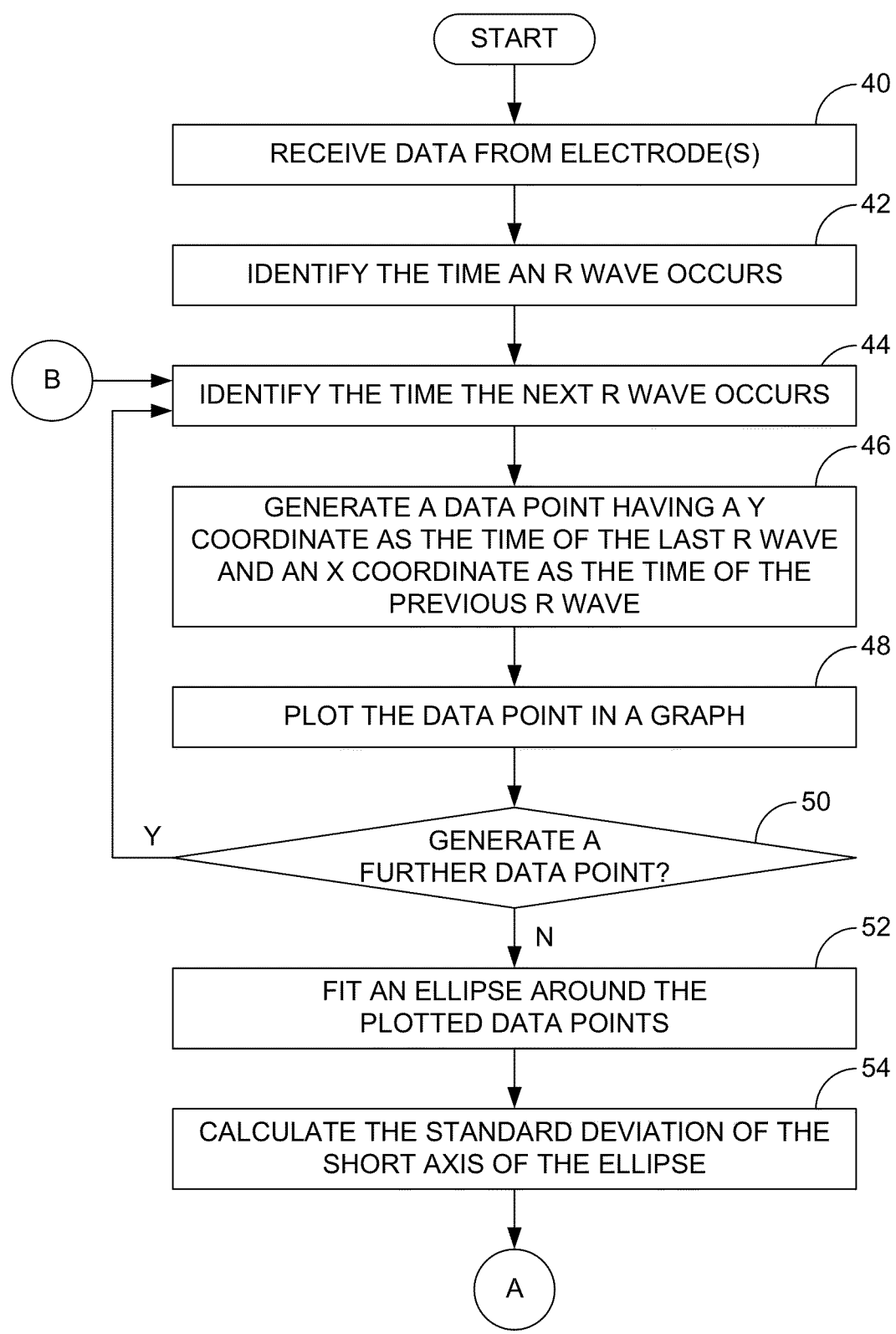
FIGS. 4A and 4B together comprise a flow diagram of an embodiment of a method for monitoring heart rate variability that can, for example, be practiced by the data collection and processing device of FIG. 2.
Figure 4B:
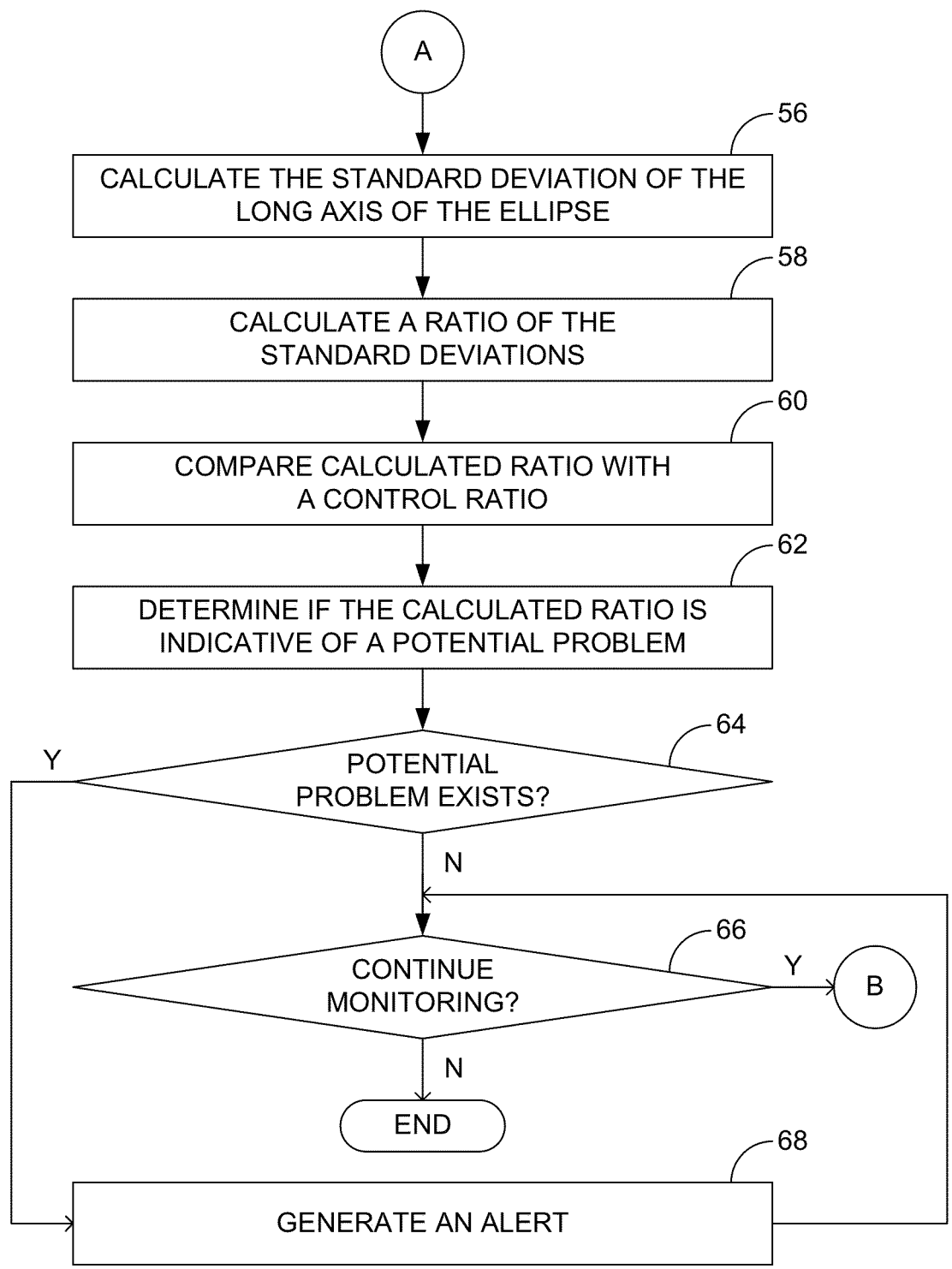

FIGS. 4A and 4B together comprise a flow diagram of a method for monitoring heart rate variability and, ultimately, health that can be performed by the data acquisition and processing device 22 by executing the heart rate variability program 30. Beginning with block 40 of FIG. 4A, heart rate data is received by the data acquisition and processing device 22 from one or more of the electrodes 16-20. In some embodiments, this data can comprise the raw QRS complex data acquired by the electrodes. Next, with reference to block 42, the data is analyzed to identify the time at which an R wave occurs. This R wave can be the first of many R waves that will be identified and used to determine the heart rate variability.

Referring next to block 44, the heart rate data is analyzed to identify the time at which the next R wave occurs. This next R wave is the R wave that immediately followed the R wave that was identified in block 42. Once the times at which the two R waves occurred have been identified, a data point can be generated, as indicated in block 46. This data point has the time of the last identified R wave as a Y coordinate and the time of the previous R wave as the X coordinate. Once this data point has been generated, the data point can be plotted on a graph that will become a Poincare plot.

At this point in the process, it is determined whether or not a further data point is to be generated, as indicated in decision block 50. Normally, the analysis is performed using multiple data points, as illustrated in FIGS. 3A and 3B. In some embodiments, a particular duration of time, such as a minute, is used as the window in which to collect data points. In such a case, the determination in decision block 50 may depend upon how long data points have been generated. Assuming that another data point is to be generated, flow returns to block 44 at which the time that the next R wave occurs is identified. In this instance, that time will be used as the new Y coordinate and the previous latest R wave time becomes the X coordinate. Therefore, a new data point is generated (block 46) and it is added to the graph (block 48).

After a suitable number of data points have been generated (e.g., after a predetermined period of time has passed), flow continues from decision block 50 to block 52 at which an ellipse is fit around the various plotted data points. In some embodiments, outlier data points can be ignored.

Once the ellipse has been generated, the standard deviation of the transverse axis and longitudinal axis of the ellipse can be calculated (blocks 54 and 56). Next, the ratio of the calculated standard deviations (e.g., SD2:SD1) can be calculated, as indicated in block 58.

At this point in the process, the calculated ratio can be compared to a control ratio that is indicative of good health, as shown in block 60. In some embodiments, the control ratio can be generated using the given user's own heart rate data taken while the user is in a healthy state to nullify the influence of variance between individuals that could skew the results. Referring next to block 62, it is then determined if the calculated ratio is indicative of a potential health problem. As noted above, if the calculated ratio deviates significantly from the healthy (control) ratio, this can be indicative of a problem. With reference to decision block 64, if the calculated ratio is indicative of a problem, an alert can be generated, as indicated in block 68. For example, the data acquisition and processing device 22 can illuminate one or more lights, emit an audible sound, vibrate, and/or generate a warning message in its display, when provided. In addition, an alert can be transmitted to an independent computing device, as described above. In some embodiments, the urgency of the alert can be commensurate with the likely severity of the user's condition. For example, if the user's normal SD2:SD1 ratio is 4:1, a message can be displayed to the user when the ratio drops to 3:1. If the ratio drops to 2:1, however, a more aggressive notification involving flashing lights, alarm sounds, and/or vibrations can be used to alert the user to the seriousness of the situation.

Whether or not a problem is detected, flow can, as indicated in decision block 66, return to block 44 for continued monitoring, or the monitoring can be terminated if monitoring is no longer desired.

It is noted that, while the above disclosure has focused on hypercapnia, the data collection and processing device 22 can additionally or alternatively be configured to determine other physiological parameters that may be useful in assessing the user's health, such as heart rate, R-R intervals, time and frequency domain heart rate variability features such as average R-R interval, standard deviation (SD) R-R interval, root mean square SD, low frequency (LF), high frequency (HF), and LF/HF. In addition, while the system has been described as being integrated into a patch that can be worn during normal daily activities, it is noted that the functionality of the system can be extended to other contexts. For example, the system can be used in a hospital context. In such a context, a patient's heart rate can be monitored using a conventional ECG system and the data collected by the system can be analyzed using a software program that resides on a computer, such as a computer in the patient's room or at a nurse's station. The software on such a computer could perform the same type of analysis described above and could issue alerts as necessary to appropriate persons, such as the patient's physician or nursing staff.

Claimed are:

1. A device for monitoring heart rate variability of a user comprising:
   a pad;
   three electrodes attached on the pad for generating heart beat data, a first electrode of the three electrodes positioned at a first corner of the pad, a second electrode of the three electrodes positioned at a second corner of the pad, a third electrode of the three electrodes positioned at a third corner of the pad such that the first electrode is configured to be positioned on a front side at a mid-axillary line within a fifth intercostal space of the user; and
   a data collection and processing device that receives the heart beat data from the three electrodes, the data collection and processing device being configured to execute a heart rate variability program configured to:
      continually determine the heart rate variability of the user in real time based upon the heart beat data by: calculating a plurality of time intervals, each time interval between two successive R waves based on the heart beat data,
      producing a plurality of data points on a map, each data point being based on two successive time intervals of the plurality of time intervals, and
      calculating the heart rate variability of a transverse axis and a longitudinal axis of one or more ellipses that contains the plurality of data points, and
      determine whether or not the user experiences hypercapnia based upon the determined heart rate variability of the transverse axis and the longitudinal axis,
      transmit a first notification in response to the heart rate variability between a length of the longitudinal axis and a length of the transverse axis being equal or lower than 3:1, and
      transmit a second notification in response to the heart rate variability being equal or lower than 2:1.

2. The device of claim 1, wherein the second electrode of the three electrodes is configured to be positioned within an upper one-half portion of a left side chest of the user,
   wherein a third electrode of the three electrodes is configured to be positioned at another upper one-half portion of the left side chest of the user.

3. The device of claim 1, wherein the pad has a rectangular shape.

4. The device of claim 3, wherein the data collection and processing device is positioned at a fourth corner of the pad.

5. The device of claim 1, wherein the data collection and processing device comprises a microprocessor, memory, and a power source.

6. The device of claim 5, wherein the data collection and processing device further comprises a wireless transmitter.

7. The device of claim 1, wherein the data collection and processing device is configured to calculate a temporal spacing of successive R wave peaks.

8. The device of claim 7, wherein the data collection and processing device is further configured to generate an ellipse to be fit around plotted data points generated from the temporal spacing of successive R wave peaks.

9. The device of claim 8, wherein the data collection and processing device is further configured to calculate the heart rate variability being as a representation of a ratio of the transverse axis and the longitudinal axis of the changing data within the ellipse.

10. The device of claim 9, wherein the data collection and processing device is further configured to compare the calculated ratio with a control ratio for the user.

11. The device of claim 10, wherein the data collection and processing device is further configured to generate an alert when the calculated ratio is outside of a predetermined range from the control ratio.

12. A method for monitoring health of a user, the method comprising:
   securing a device for monitoring heart rate variability to a chest of the user, the device comprising a pad, three electrodes integrated on the pad, and data collection and processing device, a first electrode of the three electrode being positioned on a front side at a mid-axillary line within a fifth intercostal space of the user, a second electrode of the three electrodes being positioned at an upper one-half portion of a left side chest of the user, and a third electrode of the three electrodes being positioned at another upper one-half portion of the left side chest of the user;

collecting heart rate data with the three electrodes applied to the user;

continually calculating the heart rate variability of the user in real time from the heart rate data; and determining whether or not the user experiences hypercapnia based upon the calculated heart rate variability.

13. The method of claim 12, wherein calculating the heart rate variability comprises calculating temporal spacing of successive R wave peaks to determine the heart rate variability.

14. The method of claim 13, wherein calculating the heart rate variability further comprises fitting an ellipse around data points generated from the temporal spacing of successive R wave peaks.

15. The method of claim 14, wherein calculating the heart rate variability further comprises calculating a ratio of a transverse axis and a longitudinal axis of the ellipse.

16. The method of claim 15, further comprising comparing the calculated ratio with a control ratio for the user.

17. A device for monitoring heart rate variability comprising:

an electrode configured to generate heart beat data of a user; and a data collection and processing device that receives the heart beat data from the electrode, the data collection and processing device being configured to:

continually determine the heart rate variability of the user in real time based upon the heart beat data, calculate a plurality of time intervals, each time interval between two successive R waves based on the heart beat data, producing a plurality of data points on a map, each data point being based on two successive time intervals of the plurality of time intervals, calculate a ratio of a transverse axis and a longitudinal axis of one or more ellipses that contains the plurality of data points, and determine whether or not the user has hypercapnia based on the ratio of the transverse axis and the longitudinal axis.

18. The device of claim 17, wherein the data collection and processing device is further configured:

transmit a first notification in response to the ratio between a length of the longitudinal axis and a length of the transverse axis being dropped by equal or more than 25% than the ratio of the user without having the hypercapnia.

19. The device of claim 18, wherein the data collection and processing device is further configured to:

transmit a second notification in response to the ratio dropping by 50% or more of the ratio of the user when not having hypercapnia.

20. The device of claim 19, wherein the second notification is a more aggressive notification than the first notification to indicate seriousness of the hypercapnia.

21. The device of claim 17, wherein to calculate a plurality of time intervals, the data collection and processing device is configured to calculate each time interval between peaks of the two successive R waves.

22. The device of claim 17, wherein the data collection and processing device is further configured to compare the calculated ratio with a control ratio for the user.

* * * * *